United States Patent
Kantzer et al.

(10) Patent No.: US 11,214,549 B2
(45) Date of Patent: Jan. 4, 2022

(54) PROCESS FOR MAKING HIGHER ETHYLENE AMINES

(71) Applicant: NOURYON CHEMICALS INTERNATIONAL B.V., Arnhem (NL)

(72) Inventors: Eike Nicolas Kantzer, Uddevalla (SE); Karl Fredrik Lake, Södertälje (SE); Antoon Jacob Berend Ten Kate, Arnhem (NL); Michiel Jozef Thomas Raaijmakers, Deventer (NL); Rens Veneman, Deventer (NL); Rolf Krister Edvinsson, Partille (SE); Ina Ehlers, Ödsmål (SE); Michael Bertil Einar Sarning, Gothenburg (SE); Robert Kristoffer Berg, Rönninge (SE); Hendrik Van Dam, Frölunda (SE)

(73) Assignee: NOURYON CHEMICALS INTERNATIONAL B.V., Arnhem (NL)

(*) Notice: Subject to any disclaimer, the term of this patent is extended or adjusted under 35 U.S.C. 154(b) by 0 days.

(21) Appl. No.: 16/630,283

(22) PCT Filed: Jul. 3, 2018

(86) PCT No.: PCT/EP2018/067866
§ 371 (c)(1),
(2) Date: Jan. 10, 2020

(87) PCT Pub. No.: WO2019/011708
PCT Pub. Date: Jan. 17, 2019

(65) Prior Publication Data
US 2020/0165207 A1    May 28, 2020

(30) Foreign Application Priority Data
Jul. 10, 2017 (EP) .................................... 17180568

(51) Int. Cl.
*C07D 233/34* (2006.01)
*C07C 209/78* (2006.01)

(52) U.S. Cl.
CPC .......... *C07D 233/34* (2013.01); *C07C 209/78* (2013.01)

(58) Field of Classification Search
CPC ............................ C07D 233/34; C07C 209/78
See application file for complete search history.

(56) References Cited

U.S. PATENT DOCUMENTS

| 2,812,333 | A | 11/1957 | Steele |
| 3,133,932 | A | 5/1964 | Horn et al. |
| 4,111,840 | A | 9/1978 | Best |
| 4,387,249 | A | 6/1983 | Harnden et al. |
| 4,503,250 | A | 3/1985 | Herdle |
| 4,568,745 | A | 2/1986 | Ghelli et al. |
| 4,684,729 | A | 8/1987 | Duquette et al. |
| 4,758,354 | A | 7/1988 | O'Mara et al. |
| 5,262,534 | A | 11/1993 | King |
| 5,364,971 | A | 11/1994 | Su |
| 5,491,263 | A | 2/1996 | Rooney et al. |
| 10,428,011 | B2 | 10/2019 | Edvinsson et al. |
| 2007/0100144 | A1 | 5/2007 | Frauenkron et al. |
| 2010/0029976 | A1 | 2/2010 | Dahmen et al. |
| 2010/0087681 | A1 | 4/2010 | Petraitis et al. |
| 2010/0087683 | A1 | 4/2010 | Cook et al. |
| 2010/0094007 | A1 | 4/2010 | King et al. |
| 2010/0120983 | A1 | 5/2010 | Dufaure et al. |
| 2010/0121064 | A1 | 5/2010 | Dahmen et al. |

FOREIGN PATENT DOCUMENTS

| EP | 0222934 A1 | 5/1987 |
| EP | 1654214 B1 | 3/2007 |
| EP | 2548869 A1 | 1/2013 |
| FR | 2912148 | 8/2008 |
| FR | 2912148 A1 | 8/2008 |
| GB | 1510538 | 5/1978 |
| JP | S5285991 A | 7/1977 |
| JP | S56108534 A | 8/1981 |
| JP | H01500357 A | 2/1989 |
| JP | 2012504611 A | 2/2012 |

(Continued)

OTHER PUBLICATIONS

Davis ("Thermal Degradation of Aqueous Amines Used for Carbon Dioxide Capture" Ph.D. dissertation, 2009, The University of Texas at Austin, retrieved from http://rochelle.che.utexas.edu/files/2015/02/Davis-2009-Thermal-Degradation-of-Aqueous-Amines-Used-for-Carbon-Dioxide-Capture.pdf on Feb. 10, 2019) (Year: 2009).

ISA, European Patent Office, International Search Report and Written Opinion issued in International Application No. PCT/EP2018/067866, dated Sep. 14, 2018.

ISA, European Patent Office, International Search Report and Written Opinion issued in International Application No. PCT/EP2018/067867, dated Aug. 20, 2018.

(Continued)

*Primary Examiner* — Shawquia Jackson
(74) *Attorney, Agent, or Firm* — Lorenz & Kopf, LLP

(57) ABSTRACT

Urea derivatives, methods for preparing ethylene amines, and methods of polymer manufacturing are provided. An exemplary method for preparing ethylene amines with n ethylene units and n+1 amine groups wherein n is at least 4, or urea derivatives of said ethylene amines, includes reacting an ethanolamine-functional compound, an amine-functional compound, and a carbon oxide delivering agent, wherein the ethanolamine-functional compound is of the formula HO—$(C_2H_4$-NH-$)_q$H, q is at least 1, the amine-functional compound is of the formula $H_2N$—$(C_2H_4$-NH-$)_r$H, r is at least 1, the sum q+r is at least 4 and wherein optionally one or more of the ethanol-amine functional compound or amine-functional compound are at least partly used as their cyclic carbamate derivative, or linear or cyclic urea derivative.

18 Claims, No Drawings

(56) References Cited

FOREIGN PATENT DOCUMENTS

| WO | 9749686 A1 | 12/1997 |
|---|---|---|
| WO | 2011079008 A1 | 6/2011 |
| WO | 2011107512 A1 | 9/2011 |
| WO | 2013110092 A1 | 7/2013 |
| WO | 2017137529 A1 | 8/2017 |
| WO | 2017137530 A1 | 8/2017 |
| WO | 2017137532 A1 | 8/2017 |

OTHER PUBLICATIONS

ISA, European Patent Office, International Search Report and Written Opinion issued in International Application No. PCT/EP2018/067868, dated Oct. 1, 2018.
ISA, European Patent Office, International Search Report and Written Opinion issued in International Application No. PCT/EP2018/067869, dated Sep. 14, 2018.
EPO, European Extended Search Report issued in European Patent Application No. 17180568.2, dated Oct. 13, 2017.
EPO, European Extended Search Report issued in European Patent Application No. 17180569.0, dated Jan. 22, 2018.
EPO, European Extended Search Report issued in European Patent Application No. 17180571.6, dated Jan. 22, 2018.
EPO, European Extended Search Report issued in European Patent Application No. 17180573.2, dated Jan. 22, 2018.

PROCESS FOR MAKING HIGHER ETHYLENE AMINES

CROSS-REFERENCE TO RELATED APPLICATION

This application is a U.S. National-Stage entry under 35 U.S.C. § 371 based on International Application No. PCT/EP2018/067866, filed Jul. 3, 2018, which was published under PCT Article 21(2) and which claims priority to European Application No. 17180568.2, filed Jul. 10, 2017, which are all hereby incorporated in their entirety by reference.

TECHNICAL FIELD

The present invention relates to a process for making higher ethylene amines or derivatives thereof containing at least 4 ethylene units, by reacting an ethanolamine and an ethylene amine in the presence of a carbonyl delivering agent.

BACKGROUND

There is a need to develop alternative processes by which higher ethylene amines can be manufactured.

Higher ethylene amines for the purpose of this application mean amines with n ethylene groups and n+1 amine groups, wherein n is at least 4.

Higher ethylene amines, such as tetraethylene pentamine, find their use for example in oil field applications such as disclosed WO 2011/079008 wherein tetraethylene pentamine is applied after it has been converted to a urea counterpart by reacting it with urea.

Ethylene amines consist of two or more nitrogen atoms linked by ethylene units. Ethylene amines can be present in the form of linear chains H2N(—C2H4NH)n-H. For n=1, 2, 3, 4, 5, 6 . . . these are denoted EDA, DETA, L-TETA, L-TEPA, L-PEHA, L-HEHA . . . .

With three or more ethylene units it is also possible to create branched ethylene amines such as $N(CH_2CH_2NH_2)_3$, TAEA. The moiety consisting of two adjacent nitrogen atoms linked by two ethylene units is called a piperazine ring

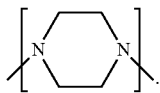

Piperazine rings can be present in longer chains to produce the corresponding cyclic ethylene amines.

Two adjacent nitrogen atoms linked by one ethylene unit and one carbonyl bridge form a cyclic ethylene urea. An ethylene amine (EA) in which two nitrogen atoms are linked intramolecularly by a carbonyl bridge

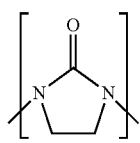

is here referred to as a UEA. Replacing the carbonyl bridge with two hydrogen atoms yields the corresponding ethylene amine. For example: EU vs EDA, UDETA vs DETA, UAEEA vs AEEA, UTETA vs L-TETA, UTEPA vs L-TEPA. Some higher amines can host more than one carbonyl bridge, e.g. DUTETA vs L-TETA. The carbonyl bridge may also link nitrogen atoms on two separate molecules—i.e. nitrogen atoms which are not linked by one ethylene unit— thereby forming a linear ethylene urea. For example, $H_2NC_2H_4NH$—CO—$NHC_2H_4NH_2$ for which replacing the carbonyl bridge with two hydrogen atoms would yield two molecules of EDA.

Each amine functional group in ethylene amines or amide functional group in ethylene ureas can be primary, secondary or tertiary. Furthermore, a secondary amine or amide can be linear—as part of a linear urea or as part of an ethylene amine group (linear secondary amines, LSA)—or cyclic (cyclic secondary amine, CSA) and a tertiary amine or amide can be branched, be part of a cyclic ethylene urea or be part of a piperazine ring.

In the presence of any Brønsted acid (such as water) ethylene amines (EA) can be protonated ($EAH^+$). If not otherwise stated the term amine in this document will include both the protonated and unprotonated form.

Some ethylene amines and urea derivatives thereof are shown below as an illustration. This can naturally be extended to include pentamines, hexamines and so on.

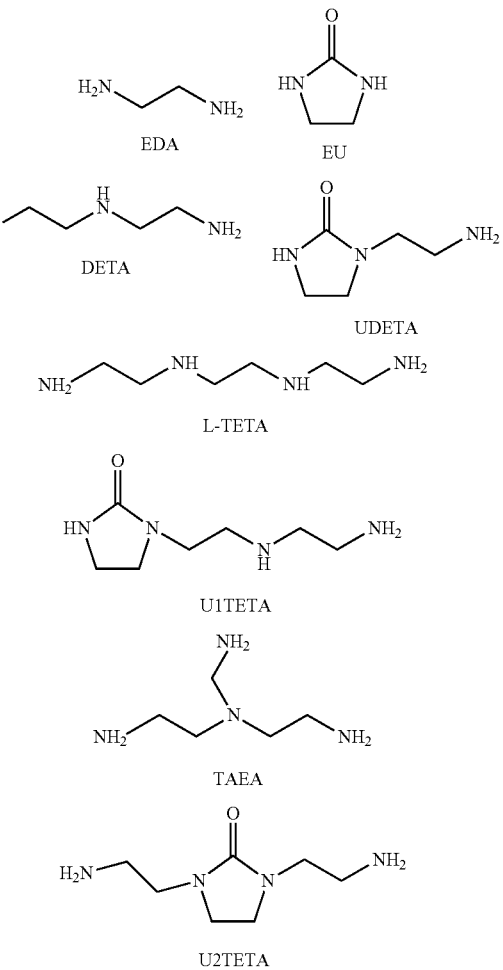

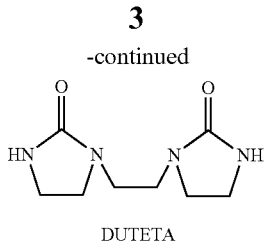

DUTETA

As to the naming of the molecules; EDA stands for ethylene diamine, DETA for diethylene triamine, TETA for triethylene tetramine, TEPA for tetraethylene pentamine, PEHA for pentaethylene hexamine, HEHA for hexaethylene heptamine. When there is a cyclic urea in the molecule this is indicated by adding a U in front of the name, i.e. UTETA means the cyclic urea of TETA, while when there are two cyclic ureas in the molecule this is indicated by DU, i.e. DUTETA means the internal cyclic diurea of TETA. If there is a number indicated with the U this refers to the amino group where the U group is located. There is one exception to this naming and that is that instead of UEDA the abbreviation EU is used, which stands for ethylene urea.

Current manufacturing processes for producing ethylene amines in general are a) the catalytic reductive amination of ethanolamines, mainly the catalytic reductive amination of 2-aminoethanol or monoethanolamine (MEA) with an excess of ammonia at temperatures around 200° C. and pressures around 200 bar and b) the reaction of EDC with ammonia at elevated temperatures and pressures to form ethylene amine hydrochlorides which are then reacted with caustic to generate mixtures of ethylene amines and NaCl.

The reductive amination of MEA proceeds in the presence of a hydrogenation/dehydrogenation catalyst and an excess of ammonia. Next to the reductive amination of MEA to give EDA a number of side reactions including transamination produce a mixture which comprises a large number of different ethylene and ethanolamines. The output is dominated by mono and diethylene products (i.e. EDA, DETA, PIP and AEEA). Higher ethylene and ethanolamines are also formed but the mixture is complex which makes this route ineffective in producing high yields of the higher ethylene amines containing at least 4 ethylene units. Therefore, the reductive amination of MEA cannot compete with the EDC route for making higher ethylene amines.

Several attempts to use transamination to produce higher/longer chains of linear ethylene amines have been reported but these seem limited to the diethylene compound DETA and therefore cannot compete with the EDC route described further below. See for example U.S. Pat. Nos. 8,383,860 B2; 8,188,318 B2; EP1654214B1 and 4,568,745.

Also processes based on nitrile chemistry are described in prior art. Nevertheless, today, the EDC-based process is the main process for producing polyethylene polyamines with at least 4 ethylene units and at least 5 amine groups.

The EDC route is the substitution reaction of EDC (ethylene dichloride) with ammonia and/or another ethylene amine at elevated temperatures and pressures to form ethylene amine hydrochlorides which are then reacted with caustic to generate mixtures of ethylene amines and NaCl.

Today, the EDC-based process is the main process for producing higher polyethylene polyamines Higher amines usually exist as so-called technical mixtures. For example, there are several possible pentamines and their technical mixture which is referred to as TEPA typically comprises a mix of linear, branched and cyclic, i.e. piperazine containing, pentamines. This can be derived from commercially available TEPA products that contain besides 50 wt % of linear TEPA, also about 15 wt % of branched TEPA and about 35 wt % of cyclic TEPAs. Also REACH registrations confirm that TEPA products now on the market contain up to 30 wt % of branched components and up to 80 wt % of cyclic components.

The EDC route apart from it being fully dependent on the use of ethylene dichloride which is toxic, highly flammable and carcinogenic, expensive, difficult to handle and therefore not always and everywhere available, has as a disadvantage that it has a low selectivity towards specific higher ethylene amines, as the process always generates a mixture of many different polyethylene polyamines of different size, and with different degrees of branching and cyclics. Furthermore the EDC route results in the creation of 2 moles of NaCl per mole EDC which in embodiment results in substantial amounts of waste, complex separation, corrosion problems and colored products thereby creating a need for additional purification steps like so-called bleaching and redistillation.

A process based on nitrile chemistry is disclosed in U.S. Pat. No. 8,440,852, but this process is disadvantageous as it needs a catalyst that contains metals like Raney nickel or cobalt. Furthermore, hydrogenation of the nitrile precursors has to be performed using highly diluted systems, employing undesired organic solvents presumably to prevent formation of unwanted by-products and to prevent premature catalyst deactivation.

GB 1510538 discloses a process for obtaining TETA and TEPA. The process involves the reaction of EDC and ammonia, followed by distillation to separate off TETA in a yield of 22% and another distillation to separate off TEPA in a yield of 12%.

U.S. Pat. No. 5,364,971 discloses a process for decoloring TETA and TEPA. Colored products in the EDC process are formed because of thermal degradation e.g. during distillation, reaction with oxygen e.g. due to leaking equipment during vacuum distillation and/or corrosion problems which are aggravated by high levels of salts, especially NaCl which is formed when NaOH is reacted with ethyleneamine hydrochlorides in the neutralization step. It is said that the TETA and TEPA compounds can be made by reacting alkanolamine, alkylene amine with ammonia or a secondary amine in the presence of a phosphorous catalyst or by reacting EDC with ammonia or reacting an alkyl halide with a diamine.

EP 222934 discloses a process to prepare polyalkylene polyamines by a modified EDC process in which the yield of TEPA is increased by reacting TETA with a mixture of EDC, ammonia and water. Examples 1-4 show the resulting product mixtures which are obtained when TETA is added to the starting materials. These results are compared to Examples A and B, where no TETA is added, in order to compare with a common EDC process. Recycling TETA in an EDC process is disadvantageous and therefore not commonly practiced because a) TETA is a valuable product in itself and thus rather isolated, b) besides TEPA also significant amounts of very high molecular polyalkylene polyamines are produced which are less desirable and c) recycling increases the residence time which increases the amount of colored products. Also a modified EDC process will probably require different equipment as the phase separation of the water, salt and ethylene amine phases after the neutralization step is strongly influenced by the composition of the ethylene amine phase.

Accordingly, there is a desire for a process that provides TEPA and higher ethylene amines in high yield and high selectivity, without using many steps like multiple recycle steps for intermediate products and without having to use expensive or hazardous starting materials, and that in addition does not lead to high amounts of high molecular ethylene amines or salts as side products and provides less colored product.

BRIEF SUMMARY

Urea derivatives, methods for preparing ethylene amines, and methods of polymer manufacturing are provided. An exemplary method for preparing ethylene amines with n ethylene units and n+1 amine groups wherein n is at least 4, or urea derivatives of said ethylene amines, includes reacting an ethanolamine-functional compound, an amine-functional compound, and a carbon oxide delivering agent, wherein the ethanolamine-functional compound is of the formula HO—(C2H4-NH-)qH, q is at least 1, the amine-functional compound is of the formula H2N—(C2H4-NH-)rH, r is at least 1, the sum q+r is at least 4 and wherein optionally one or more of the ethanol-amine functional compound or amine-functional compound are at least partly used as their cyclic carbamate derivative, or linear or cyclic urea derivative.

An exemplary method of polymer manufacturing includes using a urea derivative selected from (a) urea derivatives of pentaethylenehexamine selected from the group of 2-monourea tetraethylene pentamine, of the formula

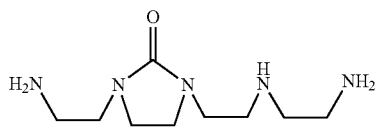 [SMILES: NCCNCCN1CCN(CCN)C1=O]

and di-urea derivatives of tetraethylene pentamines, and (b) urea derivatives of pentaethylenehexamine selected from the group of mono-urea derivatives of pentaethylene hexamine selected from the group of
1-monourea pentaethylene hexamine

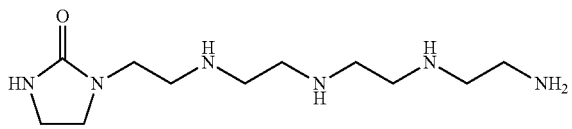 [SMILES: NCCNCCNCCNCCN1CCNC1=O]

and
2-monourea pentaethylene hexamine,

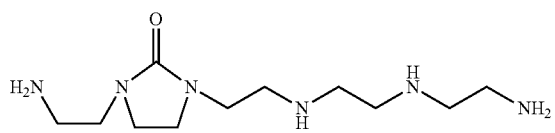 [SMILES: NCCNCCNCCN1CCN(CCN)C1=O]

and di- and tri-urea derivatives of pentaethylene hexamine.

DETAILED DESCRIPTION

The present invention now provides a process to prepare ethylene amines with n ethylene units and n+1 amine groups wherein n is at least 4, or urea derivatives of said ethylene amines, by reacting an ethanolamine-functional compound, an amine-functional compound, and a carbon oxide delivering agent, wherein the ethanolamine-functional compound is of the formula HO—(C2H4-NH-)qH, q is at least 1, the amine-functional compound is of the formula H2N—(C2H4-NH-)rH, r is at least 1, the sum q+r is at least 4 and wherein optionally one or more of the ethanol-amine functional compound or amine-functional compound are at least partly used as their cyclic carbamate derivative, or linear or cyclic urea derivative.

In comparison to the basic EDC based process the present invention has as advantages that a high yield of the higher ethylene amine of choice is obtained, with a high selectivity towards the same higher ethylene amine of choice or in embodiments single isomers of polyethylene polyamines, by choosing suitable starting materials and reaction conditions, without producing substantial amounts of other polyethylene polyamines. Furthermore the process of the present invention provides the possibility to convert even ethanolamines e.g. MEA, AEEA into polyethylene polyamines like TEPA and PEHA and requires no handling of EDC and does not result in the formation of NaCl because NaCl is not generated as by-product which in turn means that there will be less problems due to corrosion and thus the products will be less colored thereby reducing the need for additional purification steps like redistillation or bleaching.

The present invention also provides the product composition obtainable by the above process which compared to the product composition obtained by an EDC process which always produces mixtures of linear, branched and cyclic isomers, shows less branched and cyclic isomers are formed and also less lower or higher ethylene amines than the molecule that is intended.

It may be noted that U.S. Pat. No. 4,503,250 describes a process for preparing predominantly linear polyalkylene polyamines by reacting ammonia or an alkylene amine with an alcohol in the presence of a derivative of carbonic acid or carbon dioxide derivative as a catalyst. Example 5 describes the reaction of AEEA with EDA and 2-Imidazolidinone in non-catalytic amounts at 300° C. for 6 hours and subsequent hydrolysis (no time given) to yield ca. 8 wt-% L-TETA. The main component in the product mixture is the EDA starting material (76 wt. %). Example 8 shows an L-TETA yield of 8 wt. % in a reaction of 2-oxazolidinone with DETA at 275° C. for 4 hours, followed by hydrolysis. In this example, the main components in the product mixture are the DETA starting material (56 wt. %) and the EDA starting material (27 wt. %). The L-TETA yield in the other examples is even lower.

Quite unexpected, the process of the present invention at the same time not only gives a high yield but also a high selectivity for linear ethylene amines, or to phrase it differently, when the aim is to produce L-TEPA in a high yield at the same time, less branched and cyclic TEPAs are formed and also less lower or higher ethylene amines than the molecule that is intended are formed, which in the given example is TEPA.

In an embodiment of the process of the invention, the process contains an additional step wherein CO groups are removed, i.e. wherein any formed ethylene amine precursor that is a urea ethylene amine product is converted to an ethylene amine. This can be done in one embodiment by reacting with a base, such as aqueous NaOH or KOH, or by reacting with another ethylene amine, like EDA, optionally in the presence of water, and optionally while removing carbon dioxide from the reaction system.

The reaction mixture is characterized by containing as reactants an ethanolamine-functional compound, an amine-functional compound and a carbon oxide delivering agent and can be roughly represented by below non-limiting scheme.

Scheme I: Amine functional compound is a primary amine

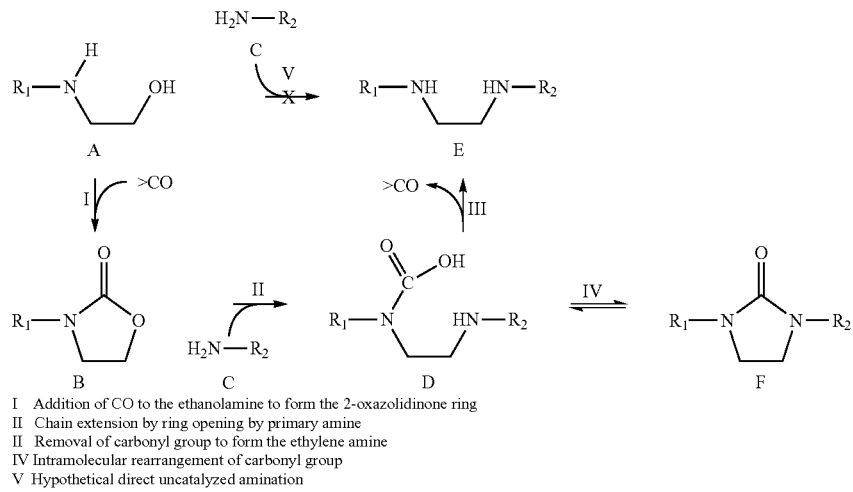

I   Addition of CO to the ethanolamine to form the 2-oxazolidinone ring
II  Chain extension by ring opening by primary amine
III Removal of carbonyl group to form the ethylene amine
IV  Intramolecular rearrangement of carbonyl group
V   Hypothetical direct uncatalyzed amination A number of reactions take place in parallel when heating a mixture of a carbon oxide source, an ethanolamine-functional compound and an amine-functional compound.

Without being bound to theory this can be summarized in two main reaction steps each composed of multiple sub steps: 1) the activation of the alcohol function (A) by the carbonyl group, the oxazolidinone (B) is assumed to be an intermediate, 2) the activated alcohol function is replaced by an amine (C) to give a chain extended primary addition product (D). In the presence of ammonia a conversion of the alcohol function to an amine function without giving a chain extension can take place as well. The product (D) may undergo further reaction leading to secondary CO containing products as illustrated by reaction IV and product (F). Such products include but are not limited to cyclic ethylene urea derivatives but include all kinds of CO containing amines as for example illustrated in below examples of CO delivering agents. Optionally, the CO groups can be removed leading to the formation of an ethylene amine (EA).

The ethanolamine-functional compound is a compound containing one hydroxyl group linked via an ethylene to an amine group that optionally may be present as its carbamate equivalent. Generally the ethanolamine-functional compound is of the following formula

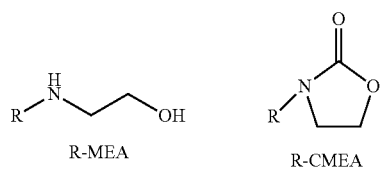

Examples of ethanolamine functional compounds include

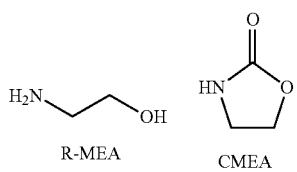

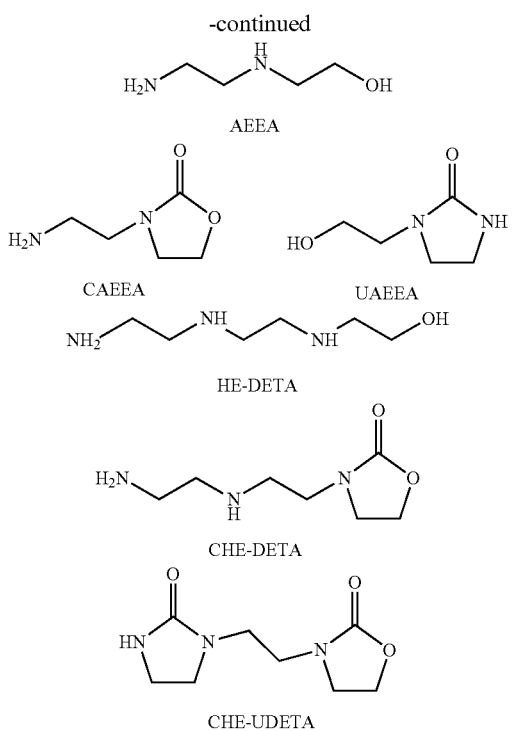

As to naming, MEA stands for monoethanolamine, AEEA stands for aminoethylethanolamine, HE-DETA for hydroxyethyldiethylene triamine, and from there on HE-TETA for hydroxyethyl triethylene tetramine etc. By using the letter C it is indicated that an internal cyclic carbamate ring is present in the molecule.

The carbon oxide delivering agent is a compound containing a carbonyl moiety that can be transferred to an ethanolamine-functional compound leading to the formation of a cyclic carbamate such as CMEA (2-oxazolidinone), or that can be transferred to an ethylene amine (EA) leading to the formation of the corresponding cyclic ethylene urea (UEA). Next to cyclic compounds linear carbamates and ureas may form as well.

Carbon oxide delivering agents within the scope of the present invention include carbon dioxide, and organic compounds in which a carbonyl group is available for being transferred as described above. Organic compounds in which a carbonyl group is available include urea and derivatives thereof; linear and cyclic alkylene ureas, especially cyclic urea, mono or di-substituted alkylene ureas, alkyl and dialkyl ureas, linear and cyclic carbamates, organic carbonates and derivatives or precursors thereof. Such derivatives or precursors may for example include ionic compounds such as carbonate or bicarbonate salts that can be converted, in some embodiments in situ in the process of the invention, into their non-ionic counterparts, for example into linear and cyclic carbamate or urea compounds. Preferably, when such ionic compounds are used in the present invention, they are organic hydrocarbon-based carbonate or bicarbonate salts. Preferably the CO delivering agent is $CO_2$ or an organic compound that is suitable for use as carbon oxide delivering agent and wherein alkylene is ethylene, or urea or ethylene carbonate, more preferably the carbon oxide delivering agent is at least partly added as carbon dioxide or urea. The carbon oxide delivering agent can be present in the process at least partly in the same molecule as the amine functional or the ethanolamine functional compound by using the aforementioned urea or carbamate compounds.

Examples of carbon oxide delivering agents include

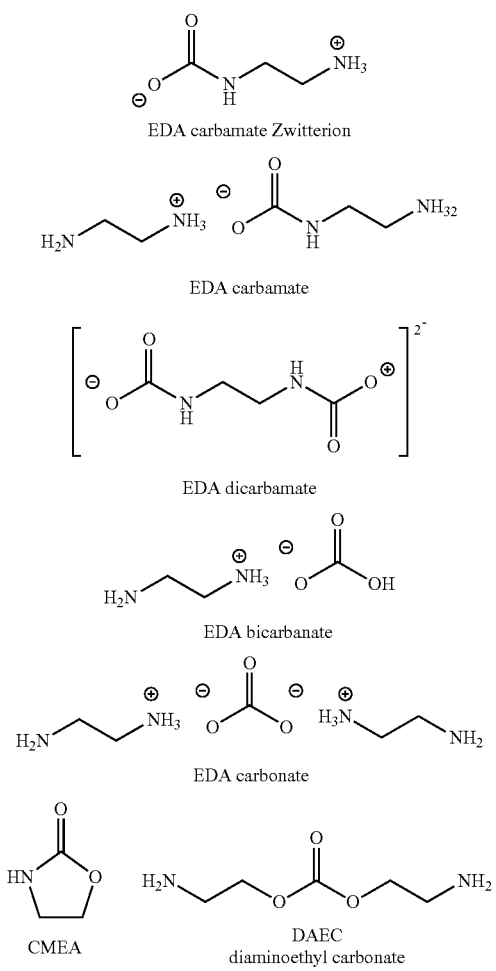

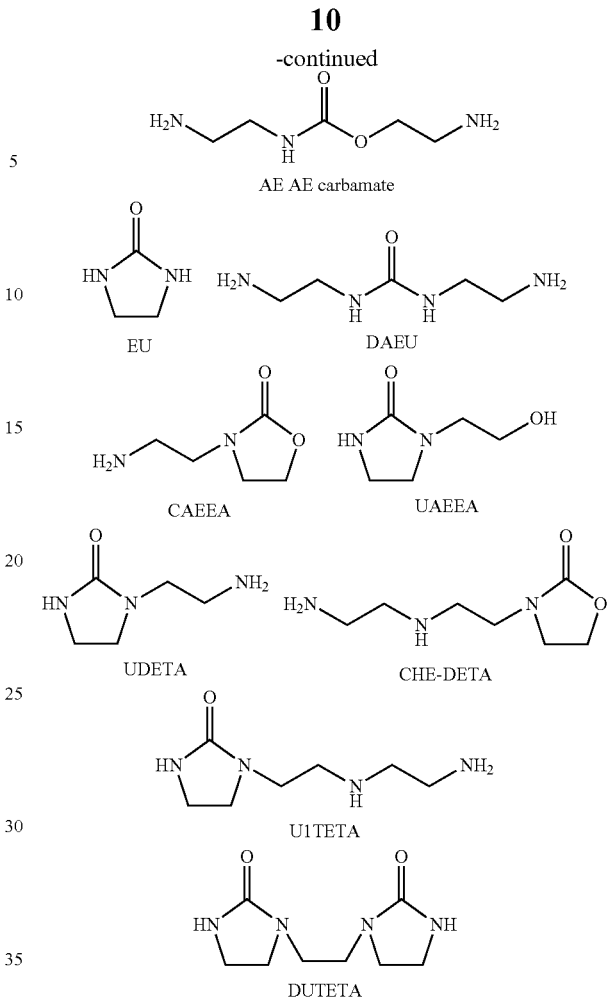

In the above drawing CAEEA again stands for the carbamate of aminoethylethanolamine, UDETA for the urea of diethylene triamine, DAEU stands for diaminoethyl urea, AE AE carbamate stands for amino ethyl aminoethanol carbamate, CHE-DETA stands for the carbamate of hydroxyethyldiethylene triamine, U1TETA stands for the urea on the first amine of triethylene tetramine, and DUTETA stands for the 1,3-diurea of triethylene tetramine.

The amine-functional compound is a compound containing at least two amine groups, and no alcohol groups wherein at least two amine groups are independently a primary amine group optionally converted into a urea group, and optionally more amine groups may be present that may be primary, secondary and/or tertiary amines wherein the amine groups within the compound are linked to one another via ethylene groups, and optionally some by a carbonyl group (to give a urea unit in the amine-functional compound).

In a further preferred embodiment in the process the ethanolamine-functional compound is of the formula HO—(C2H4-NH-)qH wherein q is at least 1 and the amine-functional compound is of the formula H2N—(C2H4-NH-)rH wherein r is at least 1, wherein the sum of q+r is 4 or 5 and wherein optionally one or more q or r units may be present as a cyclic ethylene urea and/or cyclic ethylene carbamate unit.

In another preferred embodiment the ethanolamine-functional compound and the carbon oxide delivering agent are at least partly added as one compound by using a carbamate precursor or derivative of the ethanolamine-functional compound and/or the amine-functional compound and the carbon oxide delivering agent are at least partly added as one compound by using a urea precursor or derivative of the amine-functional compound.

The carbon oxide delivering agent may be added as CO2, as a urea compound or as a carbamate compound, but preferably the CO delivering agent and the ethylene amine reactant and/or the ethanolamine reactant are present in one molecule by taking at least partly the urea or carbamate version of the ethylene amine and/or ethanolamine as reactants in the process.

When preparing TEPA or a urea precursor thereof the following preferred embodiments are covered by the process of the present invention: reacting the ethanolamine-functional compounds and amine-functional compounds MEA+TETA; AEEA+DETA; or respectively HE-DETA+EDA.

When preparing PEHA or a urea precursor thereof the following preferred embodiments are covered by the process of the present invention: Reacting the ethanolamine-functional compounds and amine-functional compounds MEA+TEPA; AEEA+TETA; HE-DETA+DETA; or respectively HE-TETA+EDA.

More preferably, in the above embodiments for preparing TEPA, PEHA or a urea precursor thereof one or more of the ethanolamine-functional compound or amine-functional compound are at least partly used as their cyclic carbamate derivative, or linear or cyclic urea derivative.

Even more preferably, in embodiments the process is about making TEPA and higher ethylene amine homologues by reacting an ethanolamine urea derivative with an ethylene amine, e.g. UAEEA+DETA, or an ethylene amine urea derivative with an ethanolamine, e.g. AEEA+UDETA, or an ethylene amine urea derivative with an ethylene amine urea derivative, e.g. UAEEA+UDETA, or mixtures of ethanolamines, ethylene amines and their respective carbamate, urea counterparts, e.g. AEEA, UAEEA, DETA and UDETA; to form urea precursors of TEPA and higher ethylene amine homologues which can then be converted into their respective ethylene amine compounds e.g. by hydrolysis with aqueous caustic.

In general, urea derivatives of ethylene amines resulting from the process according to the invention can be converted to the corresponding ethylene amines by subjecting them to hydrolysis. Processes for carrying out hydrolysis reactions are known in the art.

The urea or carbamate derivative may be obtained by reacting an ethanolamine or ethylene amine compound with urea, with CO2 and/or with another urea derivative.

In a preferred embodiment the molar ratio of carbon oxide delivering agent to amine-functional compound (also referred to as CO:amine) is higher than 1:1 and even more preferred it is higher than 1.5:1. In embodiments it is preferred that molar ratio of carbon oxide delivering agent on basis of ethylene amine product formed is lower than 1n equivalent (i.e. wherein n is the number of ethylene groups in the product made, which corresponds with the number of ethylene units (q+r) in the starting amine-functional compound and starting ethanolamine-functional compound together), even more preferably it is lower than 0.7 n equivalent and higher than 0.5 n molar equivalent.

In another preferred embodiment the molar ratio of ethanolamine-functional compound to amine-functional compound is between 1:0.1 and 1:10, preferably 1:0.3 and 1:3 and most preferably 1:0.5 and 1:2.

In another preferred embodiment for producing TEPA; the ratio (ethanolamine-functional compound to amine-functional compound) of AEEA+UAEEA+CAEEA to DETA+UDETA is lower than 10:1, yet higher than 1:10, preferably lower than 3:1, yet higher than 1:3 and most preferably lower than 2:1, yet higher than 1:2; respectively the ratio MEA+CMEA to TETA+UTETA+DUTETA is lower than 10:1, yet higher than 1:10, preferably lower than 3:1, yet higher than 1:3 and most preferably lower than 2:1, yet higher than 1:2; respectively the ratio HE-DETA+CHE-DETA+HE-UDETA+CHE-UDETA to EDA+EU is lower than 10:1, yet higher than 1:10, preferably lower than 3:1, yet higher than 1:3 and most preferably lower than 2:1, yet higher than 1:2.

In another more preferred embodiment when producing TEPA; the ratio (carbon oxide delivering agent to amine) of UAEEA+CAEEA+UDETA to UDETA+DETA is higher than 1:1, even more preferred it is higher than 1.5:1; respectively the ratio CMEA+UTETA+DUTETA to TETA+UTETA+DUTETA is higher than 1:1, even more preferred it is higher than 1.5:1; respectively the ratio CHE-DETA+EU+HE-UDETA+CHE-UDETA to EDA+EU is higher than 1:1, even more preferred it is higher than 2:1. It should be noted that any equivalent of a compound containing more than one urea and/or carbamate unit—such as e.g. DUTETA and CHE-UDETA—is considered the number of equivalents of carbon oxide delivering agent that it contains urea and/or carbamate units—i.e. 1 molar equivalent of DUTETA or CHE-UDETA is counted as 2 molar equivalents of carbon oxide delivering agent.

In another more preferred embodiment when producing PEHA; the ratio of (ethanolamine-functional compound to amine-functional compound) MEA+CMEA to TEPA+UTEPA+DUTEPA is lower than 10:1, yet higher than 1:10, preferably lower than 3:1, yet higher than 1:3 and most preferably lower than 2:1, yet higher than 1:2; respectively, the ratio of AEEA+UAEEA+CAEEA to TETA+UTETA+DUTETA is lower than 10:1, yet higher than 1:10, preferably lower than 3:1, yet higher than 1:3 and most preferably lower than 2:1, yet higher than 1:2; respectively, the ratio of HE-DETA+CHE-DETA+HE-UDETA+CHE-UDETA to DETA+UDETA is lower than 10:1, yet higher than 1:10, preferably lower than 3:1, yet higher than 1:3 and most preferably lower than 2:1, yet higher than 1:2; respectively the ratio of HE-TETA+CHE-TETA+HE-UTETA+CHE-UTETA+HE-DUTETA to EDA+EU is lower than 10:1, yet higher than 1:10, preferably lower than 3:1, yet higher than 1:3 and most preferably lower than 2:1, yet higher than 1:2.

In yet another more preferred embodiment when producing PEHA; the ratio (carbon oxide delivering agent to amine) of CMEA+UTEPA+DUTEPA to TEPA+UTEPA+DUTEPA is higher than 1:1, even more preferred it is higher than 1:1.5; respectively, the ratio of UAEEA+CAEEA+UTETA+DUTETA to TETA+UTETA+DUTETA is higher than 1:1, even more preferred it is higher than 1:1.5; respectively, the ratio of CHE-DETA+HE-UDETA+CHE-UDETA+UDETA to DETA+UDETA is higher than 1:1, even more preferred it is higher than 1:1.5; respectively the ratio of CHE-TETA+HE-UTETA+HE-DUTETA+CHE-UTETA to EDA+EU is higher than 1:1, even more preferred it is higher than 1:1.5. It should be noted that any equivalent of a compound containing more than one urea and/or carbamate unit—such as e.g. DUTETA, CHE-UDETA, HE-DUTETA and CHE-UTETA—is considered the number of equivalents of carbon oxide delivering agent that it contains urea and/or carbamate units—i.e. 1 molar equivalent of DUTETA, CHE-UDETA, HE-DUTETA or CHE-UTETA is counted as 2 molar equivalents of carbon oxide delivering agent—.

The product mixture can be further processed or fractionated into several products that each independently are either pure compounds or mixture of compounds, some of which may be recycled.

The process of the present invention can be done with or without any additional liquid present. If a liquid is added to the reaction system, the liquid preferably is a polar liquid, such as an alcohol or water. Doing the process of the present invention in the presence of water as a liquid or without any additional liquid is preferred.

The reactor employed can be any suitable reactor including continuously stirred tank reactor, pipeline reactor, tubular or multi-tubular reactor. The reactor may be adiabatic or equipped with external or internal heat exchange devices. Feed may be single point or split into multiple points. It can consist of multiple stages with inter-stage heat exchange.

The process is preferably performed at a temperature of at least 100° C. The temperature should preferably be lower than 400° C. More preferably the temperature is between 200 and 360° C. Even more preferably the temperature is between 230 and 340° C. Most preferably the temperature is between 250 and 310° C. In embodiments where the ethanolamine-functional compound is monoethanolamine the most preferred temperature range is between 230 and 290° C.

The reaction time during the process is in an embodiment at least 5 minutes, preferably at least 0.5 hours, more preferably at least 1 hour. In another embodiment the reaction time during the process is at most 40 hours, preferably at most 20 hours, more preferably at most 12 hours. The longer reaction times of more than 1 hour are especially preferred when the molar ratio of carbon oxide delivering agent to amine-functional compound is higher than 1.5:1.

The process can be carried out in a batch reactor, possibly fed-batch operation, or in a continuously operating system in one reactor or in a cascade of continuous flow reactors. The reaction and separation can be performed in separate steps or at least partially simultaneously. The reaction and separation can involve multiple reaction steps with separation steps in between.

In the large-scale production of chemicals it is preferred to employ a continuous process. The continuous process may be, for example, a single-pass or a recycle process. In a single-pass process, one or more of the reagents pass through the process equipment once, and then the resulting effluent from the reactor is sent for purification or further processing. In a preferred embodiment the process contains an additional separation step, like a short-path distillation.

The person skilled in the art is capable of selecting the proper reactor and separation unit scheme by determining the overall yield, energy consumption and waste production.

In yet another more preferred embodiment, aminoethylethanolamine (AEEA) and diethylene triamine (DETA), or MEA (monoethanolamine) and TETA (triethylene tetramine) or HE-DETA and EDA are reacted with urea or CO2 or ethylene carbonate as a carbon oxide delivering agent to form higher ethylene polyamines, mainly tetraethylene pentamine (TEPA). In the above embodiments it is possible that part of the ethanolamine-functional compounds or amine-functional compounds are already present as their derived ureas/carbamates UAEEA, CAEEA, UDETA, CMEA, UTETA, DUTETA, CHE-DETA, HE-UDETA, CHE-UDETA and/or EU.

The present invention is also directed to new urea derivatives of tetraethylene pentamine and pentaethylene hexamine. These compounds have interesting functionalities which make them suitable for use in chemical industry, e.g., as starting material or as reactive component. They can be prepared by the process described herein, wherein an ethanolamine-functional compound of the formula HO—(C2H4-NH-)qH is reacted with an amine-functional compound of the formula H2N—(C2H4-NH-)rH and a carbon oxide delivering agent, wherein q is at least 1, r is at least 1, and the total of q and r is at least 4.

It is also possible to obtain these compounds from starting materials of the above formulae wherein the total of q and r is less than 4, e.g., 3 or 2. In this case, in a first step intermediate products will be obtained containing 2 or 3 ethylene moieties, and these compounds will react to further compounds having at least 4 ethylene moieties. This means that when compounds of the present invention are to be obtained from starting materials wherein the total of q and r is less than 4, the reaction conditions, in particular the reaction time, should be selected in such a manner that the two steps required to obtain these products can take place.

In one embodiment, the present invention pertains to 2-monourea tetraethylene pentamine, of the formula

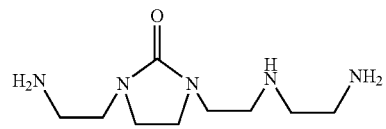

This compound combines an ethylene urea functionality with two primary amine groups and a non-cyclic secondary amine group. This combination makes for high reactivity due to the two primary amine groups, in combination with interesting functionality, due to the cyclic ethyleneurea group and the adjacent secondary amine group. This may be attractive, e.g., in the field of polymer manufacture.

In one embodiment, the present invention pertains to di-urea derivatives of tetraethylene pentamines. This pertains to the following compounds:

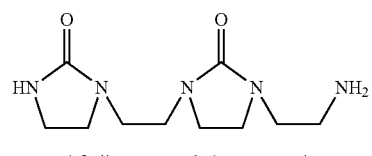

1,3-diurea tetraethylene pentamine and

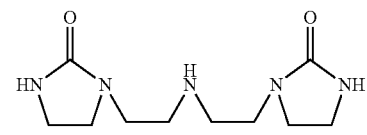

1,4-diurea tetraethylene pentamine

These compounds are attractive because they combine a dual ethylene urea moiety with a free primary or non-cyclic secondary amine. The primary or non-cyclic secondary amine makes for relatively high reactivity, while the dual urea moiety exhibits interesting properties, such as intermolecular hydrogen bonding, which can be relevant e.g., in the field of polymer manufacture.

In one embodiment, the present invention pertains to mono-urea derivatives of pentaethylene hexamine, the derivatives being selected from the group of

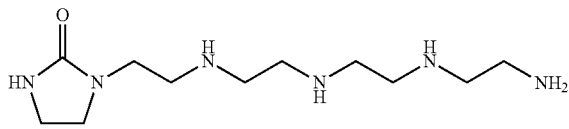

1-monourea pentaethylene hexamine and

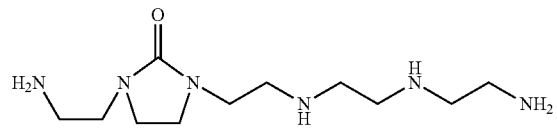

2-monourea pentaethylene hexamine

It has been found that the monourea pentaethylene hexamines where the urea group is on the 1 or 2 position of the molecule are attractive because they combine a urea moiety with a relatively long free ethylene amine tail, which can act as a spacer.

In one embodiment, the present invention pertains to a di- or tri-urea-derivative of pentaethylene hexamine.

Di- or tri-urea-derivatives of pentaethylene hexamine are compounds of the following formulae:

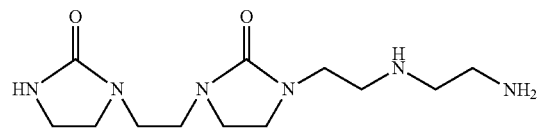

1,3-diurea pentaethylenehexamine

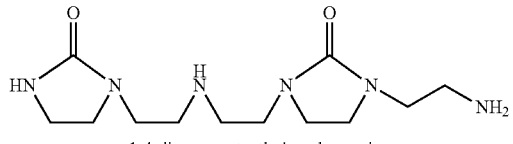

1,4-diurea pentaethylene hexamine

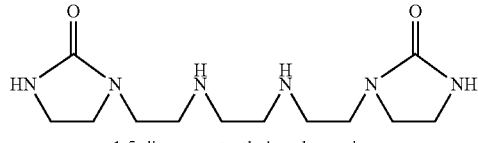

1,5-diurea pentaethylene hexamine

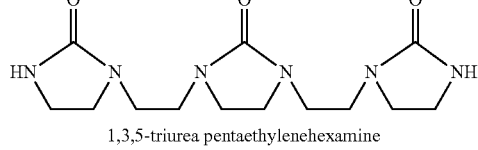

1,3,5-triurea pentaethylenehexamine

It has been found that the di- and tri-urea pentaethylene hexamine compounds which have now been made available show an attractive combination of a high number of relatively hydrophilic urea moieties in combination with a relatively long ethylene amine chain. This particular combination makes them suitable for use in chemical industry.

The present invention will be illustrated by the following examples, without being limited thereto or thereby.

EXAMPLES

In the Examples, ΣTETA stands for the sum of all TETA isomers; (U)TEPA stands for U1TEPA, U2TEPA, DUTEPA or L-TEPA; Σ(U)TEPA stands for the sum of all TEPA isomers and their urea precursors. Σ(U)PEHA, likewise, stands for the sum of all PEHA isomers and their urea precursors.

Comparative Example A: EDC Process to Prepare Higher Ethylene Amines Product Mixture (as in EP 222934 A1)

A 2 l reactor is charged with 340 g of water at ambient temperature. 20 moles (340 g) of ammonia are added. The agitator is started and the mixture heated to 130° C. Then 1 mole (60 g) of ethylenedichloride (EDC) is added. The mixture is reacted for 60 min to achieve full EDC conversion. (molar ratio of reactants, NH3:EDC=20:1)

To analyze the product mixture, excess ammonia is flashed off carefully at 40° C. Then 50% aqueous NaOH is added slowly to the reaction product. Finally NaOH pellets are added until an amine layer was formed. The amine layer is analyzed by a gas chromatograph and consists of approx. 50 wt-% L-TEPA, 15 wt-% branched TEPA and 35 wt-% cyclic TEPA. The total TEPA yield is about 4%.

Comparative Example B: EDC Process to Prepare Higher Ethylene Amines Product Mixture (as in EP 222934 A1)

The procedure of example A is employed but 272 g of water, 16 moles (272 g) of ammonia are reacted with 2 moles (198 g) of EDC (molar ratio of reactants, NH3:EDC: 8:1). For analysis the same procedure as in example A is used.

The product consists of approx. 40 wt-% L-TEPA, 15 wt-% branched TEPA and 45 wt-% cyclic TEPA. The total TEPA yield is about 8%.

Examples 1 to 7

In below Examples 1 to 6 the following compounds were used
UAEEA: 1-(2-hydroxyethyl)imidazolidin-2-one
DETA: 2,2'-Diaminodiethylamine (Diethylenetriamine)
UDETA: 1-(2-aminoethyl)imidazolidin-2-one
L-TETA: N,N'-Bis(2-aminoethyl)ethane-1,2-diamine (Triethylenetetramine)
DUTETA: 1,1'-(ethane-1,2-diyl)bis(imidazolidin-2-one)

Example 1

Process to Prepare (U)TEPA by Reacting UAEEA and DETA

UAEEA (10.0 g, 77 mmol) and DETA (7.9 g, 77 mmol) were added to a 45 mL Parr pressure autoclave. The molar ratio of carbon oxide delivering agent to ethyleneamine compound is thus 1:1 and the molar ratio of ethanolamine compound (UAEEA) to ethylene amine (DETA) compound is 1:1. The autoclave was put under an atmosphere of N₂ (3.3 bar, three cycles). The autoclave was heated to an internal temperature of 270° C. during a ramping period of 60 min and was then heated at 270° C. for 5 h. The pressure increased to 9.5 bar. The reactor was cooled to ambient temperature and was weighed out to confirm that no mass had been lost. A yellowish mixture was obtained which was analyzed by GC-FID using an internal standard. The yield of TEPA produced in this Example was comparable to the yield as obtained using the EDC process as in Comparative Example B but unlike in Comparative Example B TETA was not produced in a detectable amount, which means that the product selectivity to TEPA is higher which is a real advantage. Furthermore in Comparative Examples A and B—next to L-TEPA—also branched and piperazine-containing isomers are formed while the reaction of UAEEA and DETA in this Example 1 yields ureas of solely L-TEPA, i.e. not containing branched or piperazine-containing TEPA isomers.

Example 2

Process to Prepare TEPA by Reacting UAEEA, UDETA and DETA

UAEEA (6.0 g, 46 mmol), DETA (1.9 g, 19 mmol) and UDETA (9.0 g, 65 mmol) were added to a 45 mL Parr pressure autoclave. The total amount of carbon oxide delivering agent (total U compounds) is 111 mmol (46 mmol+65 mmol) to 84 mmol (19 mmol+65 mmol) ethylene amine (DETA+UDETA) compound, i.e. a molar ratio of carbon oxide delivering agent to ethylene amine-functional compound of 1.3:1 was used and the molar ratio of ethanolamine compound (UAEEA) to ethylene amine (DETA+UDETA) compound is 46 mmol to 84 mmol, i.e. a molar ratio of 0.55 (i.e. 1:1.8). The autoclave was put under an atmosphere of $N_2$ (4.5 bar, three cycles). The autoclave was heated to an internal temperature of 270° C. during a ramping period of 60 min and was then heated at 270° C. for 10 h. The reactor was cooled to ambient temperature and was weighed out to confirm that no mass had been lost. A yellowish mixture was obtained which was analyzed by GC-FID using an internal standard.

Example 3

Process to Prepare (U)TEPA by Reacting UAEEA and UDETA

UAEEA (10.0 g, 77 mmol) and UDETA (10.7 g, 77 mmol) were added to a 45 mL Parr pressure autoclave. The total amount of carbon oxide delivering agent (total U compounds) is 154 mmol (77 mmol+77 mmol) to 77 mmol ethylene amine (UDETA) compound, i.e. a molar ratio of carbon oxide delivering agent to ethylene amine-functional compound of 2:1 was used and the molar ratio of ethanolamine compound (UAEEA) to ethylene amine (UDETA) compound is 77 mmol to 77 mmol, i.e. a molar ratio of 1:1. The autoclave was put under an atmosphere of N2 (3.5 bar, three cycles). The autoclave was heated to an internal temperature of 270° C. during a ramping period of 60 min and was then heated at 270° C. for 5 h. The pressure increased to 9.0 bar. The reactor was cooled to ambient temperature and was weighed out to confirm that no mass had been lost. A yellowish mixture was obtained which was analyzed by GC-FID using an internal standard.

Example 4

Process to Prepare (U)TEPA by Reacting UAEEA and DETA

UAEEA (8.0 g, 62 mmol), UDETA (8.8 g, 62 mmol, 92.8% assay) and DETA (1.6 g, 15 mmol) were added to a 45 mL Parr pressure autoclave. The total amount of carbon oxide delivering agent (total U compounds) is 124.0 mmol (62 mmol+62 mmol) to 77 mmol ethylene amine (UDETA+DETA) compound, i.e. a molar ratio of carbon oxide delivering agent to ethylene amine-functional compound of 1.6:1 was used and the molar ratio of ethanolamine compound (UAEEA) to ethylene amine (UDETA+DETA) compound is 62 mmol to 77 mmol (62 mmol+15 mmol), i.e. a molar ratio of 1:1.2. The autoclave was put under an atmosphere of N2 (4.5 bar, three cycles). The autoclave was heated to an internal temperature of 270° C. during a ramping period of 60 min and was then heated at 270° C. for 8 h. The pressure increased to 14 bar. The reactor was cooled to ambient temperature and was weighed out to confirm no mass loss. A brown mixture was obtained which was analyzed by GC-FID using an internal standard.

The results obtained in comparative Examples A and B and Examples 2 to 4 are summarized in below Table 1. Table 1 clearly shows that the process of the present invention gives a different product mixture containing predominantly the desired TEPA products and no measurable amount of the higher ethylene amine TETA as is the case in Example A and B and furthermore, when the CO:amine molar ratio is higher than 1:1, as in Examples 2 to 4, that the selectivity and yield can be further improved by optimizing the ratios between the reactants.

TABLE 1

| | (Comparative) Examples | | | | |
|---|---|---|---|---|---|
| | A (comparative EDC process) | B (comparative EDC process) | 2 | 3 | 4 |
| Reaction temperature | 130° C. | 130° C. | 270° C. | 270° C. | 270° C. |
| Reaction time | 0.5 h | 0.5 h | 10 h | 5 h | 8 h |
| CO:amine molar ratio in reactants | — | — | 1.3:1 | 2:1 | 1.6:1 |
| Ethanolamine:amine molar ratio in reactants | — | — | 1:1.8 | 1:1 | 1:1.2 |
| Products | | | | | |
| EDA | 55.3 | 42.5 | n.d. | n.d. | 0.5 |
| AEEA | — | — | 2.0 | 0.7 | 1.2 |
| UAEEA | — | — | 8.8 | 22.8 | 9.8 |
| DETA | 23.3 | 24.1 | 5.3 | 0.5 | 2.3 |

TABLE 1-continued

| | (Comparative) Examples | | | | |
|---|---|---|---|---|---|
| | A (comparative EDC process) | B (comparative EDC process) | 2 | 3 | 4 |
| UDETA | — | — | 43.8 | 33.1 | 34.3 |
| PIP | 1.9 | 1.4 | 0.7 | n.d. | 0.8 |
| U1TEPA | | | 3.4 | n.d. | 1.6 |
| U2TEPA | | | 1.9 | n.d. | 1.7 |
| DU1,3TEPA | | | 7.0 | 8.1 | 16.5 |
| DU1,4TEPA | | | 7.3 | 13.7 | 4.9 |
| ΣTETA | 9.9 | 13.9 | n.d. | n.d. | 1.2 |
| Σ(U)TEPA | 3.9 | 7.7 | 19.6 | 21.8 | 24.7 |
| Highers | 2.3 | 7.6 | 0.9 | 1.4 | 1.1 |
| Normalized. Σ(U)TEPA yield | 4.0 | 7.9 | 24 | 26 | 31 |

All yields in wt-%
n.d. = not detectable (below detection limit)
Highers = Ethylene amines and derivatives with higher molecular weights than TEPA
ΣTETA = Sum of TETA compounds
Σ(U)TEPA = Sum of TEPA compounds and TEPA urea derivatives
U1TEPA is 1-monourea tetraethylenepentamine
U2TEPA is 2-monoure tetraethylenepentamine
DU1,3TEPA is 1,3-diurea tetraethylenepentamine
DU1,4TEPA is 1,4-diurea tetraethylenepentamine Example 5

Hydrolysis of Product Mixture of Example 4

The reaction mixture from Example 4 (3.0 g), NaOH (3.0 g) and water (12.0 g) were added to a Parr pressure autoclave. The autoclave was put under an atmosphere of $N_2$ (3.4 bar, three cycles). The autoclave was heated to an internal temperature of 200° C. during a ramping period of 60 min and was then heated at 200° C. for 4 h. The reactor was cooled to ambient temperature and was weighed out to confirm that no mass had been lost. The resulting mixture was analysed by GC-FID and found to contain L-TEPA.

Example 6

Process to Prepare (U)PEHA by Reacting UAEEA, DUTETA and L-TETA

UAEEA (8.0 g, 61.5 mmol), DUTETA (3.0 g, 15.37 mmol) and L-TETA (7.0 g, 46.1 mmol) were added to a 45 mL Parr pressure autoclave. The total amount of carbonyl delivering agent (total U compounds) is 92.24 mmol (61.5 mmol+2*15.37 mmol) to 61.47 mmol (15.37 mmol+46.1 mmol) ethylene amine (DUTETA+L-TETA) compound, i.e. a molar ratio of carbonyl delivering agent to ethanolamine-functional compound of 1.50:1 was used and the molar ratio of ethanolamine compound (UAEEA) to ethylene amine (DUTETA+L-TETA) compound is 61.5 mmol to 61.47 mmol (15.37 mmol+46.1 mmol), i.e. a molar ratio of 1:1. The autoclave was put under an atmosphere of N2 (4.2 bar, three cycles). The autoclave was heated to an internal temperature of 270° C. during a ramping period of 60 min and was then heated at 270° C. for 5 h. The pressure increased to 7.5 bar. The reactor was cooled to ambient temperature and was weighed out to confirm that no mass had been lost. A grayish slurry was obtained which was analyzed by GC-FID using an internal standard. The results are summarized in below Table 2.

TABLE 2

| Example 6 | |
|---|---|
| Reaction temperature | 270° C. |
| Reaction time | 5 h |
| CO:amine molar ratio in reactants | 1.50:1 |
| Ethanolamine:amine molar ratio in reactants products | 1:1 |
| AEEA | 12.4 |
| UAEEA | 13.5 |
| PIP | 0.40 |
| L-TETA | 6.9 |
| U1TETA | 17.0 |
| U2TETA | 9.2 |
| DUTETA | 13.0 |
| L-TEPA | n.d. |
| UTEPA | n.d. |
| DUTEPA | n.d. |
| L-PEHA | n.d. |
| UPEHA | n.d. |
| DUPEHA | 11.8 |
| TUPEHA | 0.2 |
| Σ(U)PEHA | 12.0 |
| Normalized. Σ(U)PEHA yield | 14.2 |

All yields in wt-%
n.d. = not detectable (below detection limit)
Σ(U)PEHA = Sum of PEHA compounds and PEHA urea derivatives Example 7

Process to Prepare (U)TEPA by Reacting $CO_2$, AEEA and DETA

AEEA (8.8 g, 85 mmol) and DETA (10.5 g, 102 mmol) were added to a 45 mL Parr pressure autoclave under an atmosphere of nitrogen. $CO_2$ (gaseous, 7.2 g, 165 mmol) was introduced to the vessel. The total amount of carbon oxide delivering agent is 165 mmol to 102 mmol ethylene amine (DETA) compound, i.e. a molar ratio of carbon oxide delivering agent to ethylene amine-functional compound of 1.6:1 was used and the molar ratio of ethanolamine compound (AEEA) to ethylene amine (DETA) compound is 85 mmol to 102 mmol, i.e. a molar ratio of 1:1.2. The autoclave was heated to an internal temperature of 240° C. during a ramping period of 50 min and was then heated at 240° C. for 2 h. The reactor was cooled to 90° C. and the volatiles (mainly water) were removed at ca 10 mbar during 30 minutes. Nitrogen gas was introduced and the autoclave was heated to an internal temperature of 270° C. during a ramping period of 50 min and was then heated at 270° C. for 8 h. A yellowish mixture was obtained which was analyzed by GC-FID using an internal standard. The results are presented in Table 3.

TABLE 3

| Example 7 | |
| --- | --- |
| Reaction temperature | 270° C. |
| Reaction time | 8 h |
| CO:amine molar ratio in reactants | 1.6:1 |
| Ethanolamine:amine molar ratio in reactants | 1:1.2 |
| Products | |
| EDA | 0.3 |
| AEEA | 0.7 |
| UAEEA | 7.8 |
| DETA | 1.2 |
| UDETA | 24.8 |
| PIP | 0.4 |
| U1TEPA | 1.6 |
| U2TEPA | 1.5 |
| DU1,3TEPA | 13.0 |
| DU1,4TEPA | 6.6 |
| Σ(U)TETA | 3.0 |
| Σ(U)TEPA | 23.0 |
| Highers | n.d. |
| Normalized. Σ(U)TEPA yield | 33.0 |

All yields in wt-%
n.d. = not detectable (below detection limit)
Highers = Ethylene amines and derivatives with higher molecular weight than TEPA
ΣTETA = Sum of TETA compounds
Σ(U)TEPA = Sum of TEPA compounds and TEPA urea derivatives
U1TEPA is 1-monourea tetraethylenepentamine
U2TEPA is 2-monourea tetraethylenepentamine
DU1,3TEPA is 1,3-diurea tetraethylenepentamine
DU1,4TEPA is 1,4-diurea tetraethylenepentamine While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for preparing ethylene amines with n ethylene units and n+1 amine groups wherein n is at least 4, or urea derivatives of said ethylene amines, the method comprising:
reacting an ethanolamine-functional compound, an amine-functional compound, and a carbon oxide delivering agent, wherein the ethanolamine-functional compound is of the formula $HO-(C_2H_4-NH-)_qH$, q is at least 1, the amine-functional compound is of the formula $H_2N-(C_2H_4-NH-)_rH$, r is at least 1, the sum q+r is at least 4.

2. The method according to claim 1 wherein the molar ratio of ethanolamine-functional compound to amine-functional compound is from about 1:0.1 to about 1:10.

3. The method according to claim 1, wherein the molar ratio of carbon oxide delivering agent to amine-functional compound is higher than about 1:1.

4. The method according to claim 1 wherein the molar ratio of carbon oxide delivering agent to amine-functional compound is higher than about 1.5:1.

5. The method according to claim 1 wherein the ethanolamine-functional compound and the carbon oxide delivering agent are at least partly added as one compound by using a carbamate precursor or derivative of the ethanolamine-functional compound.

6. The method according to claim 1 wherein the amine-functional compound and the carbon oxide delivering agent are at least partly added as one compound by using a urea precursor or derivative of the amine-functional compound.

7. The method according to claim 1 wherein the carbon oxide delivering agent is at least partly added as carbon dioxide or urea.

8. The method according to claim 1 further comprising converting the obtained ethylene urea at least partly into its corresponding ethylene amine via hydrolysis.

9. The method according to claim 1 wherein the sum q+r is 4 or 5.

10. The method according to claim 1 wherein the ethanolamine-functional compound and the amine functional compound are respectively:

monoethanolamine (MEA)+triethylenetetramine (TETA); aminoethylethanolamine (AEEA)+diethylenetriamine (DETA); or hydroxyethyldiethylenetriamine (HE-DETA)+ethylenediamine (EDA) to react to the ethylene amine tetraethylenepentamine (TEPA) or a urea derivative thereof, or wherein the ethanolamine-functional compound and the amine functional compound are respectively:

monoethanolamine (MEA)+tetraethylenepentamine (TEPA); aminoethylethanolamine (AEEA)+triethylenetetramine (TETA); hydroxyethyldiethylenetriamine (HE-DETA)+diethylenetriamine (DETA); or hydroxyethyltriethylenetetramine (HE-TETA)+ethylenediamine (EDA) to react to the ethylene amine pentaethylenehexamine (PEHA) or urea derivative thereof.

11. The method of claim 9, wherein one or more of the ethanol-amine functional compound or amine-functional compound are at least partly used as their cyclic carbamate derivative, or linear or cyclic urea derivative.

12. The method of claim 1 wherein a selected urea derivative of pentaethylenehexamine is selected from the group of 2-monourea tetraethylene pentamine, of the formula

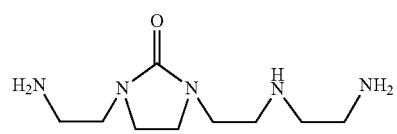 [SMILES: NCCNCCN1CCN(CCN)C1=O]

and di-urea derivatives of tetraethylene pentamines.

13. The method of claim 1 wherein a selected urea derivative of pentaethylenehexamine is selected from the group of mono-urea derivatives of pentaethylene hexamine selected from the group of

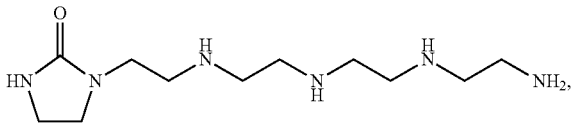

1-monourea pentaethylene hexamine and

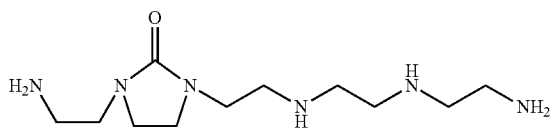

2-monourea pentaethylene hexamine and di- and tri-urea derivatives of pentaethylene hexamine.

14. The method of claim 1 wherein one or more of the ethanol-amine functional compound or amine-functional compound are at least partly used as their cyclic carbamate derivative, wherein the cyclic carbamate derivative is selected from the carbamate of aminoethylethanolamine (CAEEA), amino ethyl aminoethanol carbamate (AE AE carbamate), carbamate of hydroxyethyldiethylene triamine (CHE-DETA).

15. The method of claim 1 wherein one or more of the ethanol-amine functional compound or amine-functional compound are at least partly used as their linear urea derivative.

16. The method of claim 1 wherein one or more of the ethanol-amine functional compound or amine-functional compound are at least partly used as their cyclic urea derivative.

17. The method of claim 1 wherein one or more of the ethanol-amine functional compound or amine-functional compound are at least partly used as their linear or cyclic urea derivative.

18. The method of claim 1 wherein one or more of the ethanol-amine functional compound or amine-functional compound are at least partly used as their urea derivative selected from ethylene urea (EU), the cyclic urea of triethylene tetramine (UTETA), the internal cyclic diurea of triethylene tetramine (DUTETA), the urea of diethylene triamine (UDETA), the urea on the first amine of triethylene tetramine (U1TETA), and the 1,3-diurea of triethylene tetramine (DUTETA).

* * * * *